United States Patent [19]
Kunz et al.

[11] Patent Number: 5,478,732
[45] Date of Patent: Dec. 26, 1995

[54] PROCESS FOR THE PREPARATION OF LONG-CHAIN INULIN WITH INULINASE

[75] Inventors: Markwart Kunz, Braunschweig; Mohammed Munir, Kindenheim; Manfred Vogel, Neuleiningen, all of Germany

[73] Assignee: Sudzucker AG, Mannheim/Ochsenfurt, Germany

[21] Appl. No.: 243,789

[22] Filed: May 17, 1994

[30] Foreign Application Priority Data

May 17, 1993 [DE] Germany ............... 43 16 425.0

[51] Int. Cl.$^6$ ................ C12P 19/04; C12S 3/02; C08B 37/18
[52] U.S. Cl. ............... 435/101; 536/123.1; 536/124; 536/127; 536/128
[58] Field of Search ............ 435/101; 536/123.1, 536/124, 127, 128

[56] References Cited

U.S. PATENT DOCUMENTS

| | | | |
|---|---|---|---|
| 2,782,123 | 2/1957 | Rubin | 426/549 |
| 4,758,515 | 7/1988 | Bärwald et al. | 435/99 |
| 4,978,751 | 12/1990 | Biton et al. | 536/123 |
| 5,127,956 | 7/1992 | Hansen et al. | 127/42 |
| 5,254,174 | 10/1993 | Hansen et al. | 127/53 |
| 5,342,631 | 8/1994 | Yatka et al. | 426/3 |

FOREIGN PATENT DOCUMENTS

| | | |
|---|---|---|
| 0043169 | 6/1982 | European Pat. Off. |
| 0429077A2 | 5/1991 | European Pat. Off. |
| 60-160893 | 8/1985 | Japan |

OTHER PUBLICATIONS

The Merck Index (11th Ed., 1989) p. 792.

Primary Examiner—David M. Naff
Assistant Examiner—Francisco C. Prats
Attorney, Agent, or Firm—Finnegan, Henderson, Farabow, Garrett & Dunner

[57] ABSTRACT

A process for the preparation of long-chain inulin having an average chain length greater than 20 monomer units while simultaneously obtaining glucose and fructose is performed. An aqueous crude inulin suspension with a crude inulin concentration of 20–70% by weight is subjected to enzymatic treatment with inulinase at temperatures of 30°–70° C. During the process the short-chain components are degraded to mono- and disaccharides, and the long-chain inulins are then separated off from the mono- and disaccharides and converted into dry form. The long chain inulins may be separated from the mono- and disaccharides by crystallization by cooling and centrifugation or chromatographically using a strongly acidic cation exchange resin loaded with calcium ions. The long chain inulins can be used as a component in foodstuffs, in conjunction with sweeteners, bulking agents, thickeners, stabilizers, as well as a fat substitute in foodstuffs, a carbohydrate substitute, dietary fiber, as an excipient for pharmacologically active substances, and as an indicator for kidney clearance.

9 Claims, No Drawings

PROCESS FOR THE PREPARATION OF LONG-CHAIN INULIN WITH INULINASE

BACKGROUND OF THE INVENTION

The invention relates to the preparation of long-chain inulin from plant extracts while simultaneously obtaining glucose and fructose.

Inulin is a polysaccharide belonging to the group of the fructans. Economically obtainable amounts are found in a series of plants, such as Jerusalem artichoke tubers and dahlia tubers, and also in chicory roots. It is a heterofructan since a β-1,2-linked chain of fructose molecules is terminated by an α-D-glucose at the reducing end. The chain length depends both on the plant species and on the growth stage of the plant.

It is known (F. Perschak and L. Wolfslehner, Zuckerind., 115 (1990) 466–470) to extract inulin from the plant tissue using hot water, to remove the salts from the extract, to decolorize it and to obtain inulin from the product in dry form. This inulin, which contains monosaccharides, such as glucose and fructose, and disaccharides, such as sucrose and fructo-oligosaccharides in addition to the polymeric component, is used as a raw material for the preparation according to the invention of long-chain inulin. It will be termed "crude inulin" hereinbelow.

In contrast, DE-A 4,003,140 discloses the enzymatic cleavage of inulins to give shorter chains and the use of the fraction of a degree of polymerization of approximately 3–7 as calorie-reduced sugar substitutes which are suitable for diabetics.

Because of its mono- and disaccharide content, the crude inulin is unsuitable for the preparation of dietetic foodstuffs, in particular those intended for diabetics. Also, due to the hygroscopicity and tackiness of the short-chain oligosaccharides, they can be very troublesome when crude inulin is used in foodstuffs both in processing and in storing.

The sweet taste of the short-chain oligosaccharides in the crude inulin is troublesome for a series of applications in the food sector (for example meat products). Since long-chain inulin has a neutral flavor, it is better suited for such uses than crude inulin.

Due to the mono- di- and oligosaccharide content of crude inulin, its chemical or biochemical conversion also only gives undefined product mixtures whose purification is virtually impossible.

It is therefore desirable to obtain, by removal of the short-chain oligosaccharides, an inulin product from the crude inulin which has only long-chain molecules. Short-chain oligosaccharides are also to be understood as including molecules which have degrees of polymerization (DP) of up to 10–12. Accordingly, long-chain inulin is virtually free from the molecules of DP<10–12 and therefore has, in the case of chicory inulin, an average chain length of >20.

A series of processes is suitable for the preparation of such a long-chain inulin.

Long-chain inulin can be precipitated under suitable conditions from an aqueous solution in the presence of high concentrations of organic solvents, such as methanol, ethanol, isopropanol or their mixtures and then isolated using a centrifuge or pressure filter. On the other hand, the disadvantage of this process is that it involves organic solvents whose use is especially problematic, particularly in the food sector. On the other hand, the process involves large volumes, which means that the dissolved components which have been separated off, such as glucose, fructose, sucrose and oligosaccharides have to be recovered from dilute solutions and the yield of the desired long-chain inulins is low due to losses caused by dissolution.

Aqueous inulin solutions can also be subjected directly to crystallization with an addition of seed crystals, so that mainly long-chain inulins are precipitated and can be removed by centrifugation. However, the resulting products are relatively badly contaminated with the accompanying substances, in particular the short-chain inulins. In this process, too, a large proportion of the higher inulins remain in the mother liquor and are thus lost.

BE 92/010921 (unpublished) discloses the removal of low-molecular-weight components of up to approximately DP 5 by means of chromatographic separation of the inulin. In this case, the resulting inulin is contaminated with substantial amounts of short-chain molecules due to the poor separating effect and thus has a low mean chain length.

Application WO 91/18000 describes a process for obtaining oligosaccharides from biomass by means of ultrafiltration. However, the use of this process for the separation of inulin involves some serious disadvantages. The mono- and disaccharides and short-chain oligosaccharides are obtained in the permeate in extremely dilute solutions and can only be recovered with a high input of energy. The membranes are expensive and furthermore only have short working lives. Moreover, they tend to foul readily.

It was therefore an object to find a novel process for the preparation of long-chain inulins which avoids the disadvantages of the known processes.

SUMMARY OF THE INVENTION

The object is achieved by providing a process for the preparation of long-chain inulin while simultaneously obtaining glucose and fructose, which comprises subjecting an aqueous crude inulin suspension with a crude inulin concentration of 20–70% by weight to an enzymatic treatment with hydrolase at temperatures of 30°–70° C., during which process the short-chain components are degraded to mono- and disaccharides, and the long-chain inulins are separated off from the mono- and disaccharides in the resulting suspension and converted into dry form.

Surprisingly, the treatment of a crude inulin suspension with suitable hydrolases under certain conditions leads to a product which, in addition to long-chain inulin, virtually only contains glucose and fructose, i.e. which is substantially free from short-chain oligosaccharides. This product can be separated on an industrial scale either by chromatography, ultrafiltration or crystallization into a fraction which only contains long-chain inulin, a mixed fraction of glucose and fructose and a fructose fraction of high purity. This means that not only the desired long-chain inulin, but also fructose as a valuable by-product are obtained in high purity.

The principle of the process according to the invention, i.e. enzymatic degradation in a suspension of the medium-sized and short chains, most of which are dissolved, while not cleaving the sparingly soluble constituents, is not limited to inulin, but can also be applied as desired to other polysaccharides in which longer-chain products are to be separated off from the shorter-chain products.

DETAILED DESCRIPTION OF THE INVENTION

In the extraction of inulin-containing plant material, such as chicory roots or dahlia and Jerusalem artichoke tubers, extracts are obtained which always contain the entire range of monomeric to polymeric carbohydrates. Most of the low-molecular-weight carbohydrates are already present in the plant material, but can also be formed additionally in some cases during the extraction and the removal of salts from the extract. The solubility of these carbohydrates depends, on the one hand, on the temperature and decreases, on the other hand, with increasing chain length. According to the invention, the crude inulin solution is concentrated until a suspension is formed which can still be processed, i.e. pumped or stirred. In this manner, for example, suspensions with a crude inulin content of 40% by weight can be processed without problem at 50° C. By increasing the temperature to 60° C., the crude inulin concentration can be increased to 50%. Even though this results in a thicker consistency, the suspension can still be processed readily.

Depending on the stability at high temperatures, crude inulin contents of 20 to 70% by weight, preferably 40–50% by weight, are useful. At a suitable temperature and concentration, such crude inulin suspensions contain all mono-, di- and oligomeric carbohydrates in dissolved form and the long-chain inulin in suspended form.

In a preferred, but not limiting embodiment of the process according to the invention, a crude inulin suspension is prepared by first preparing a clear solution at 80°–100° C. which contains 20–70% by weight of crude inulin, slowly cooling this solution to 30°–70° C., preferably 40°–60° C., and holding the resulting suspension for 2–48 hours at this last-mentioned temperature. The cooling rate is in this case, for example, 0.1–2.5 Kh$^{-1}$. Other processes for the preparation of such suspensions are, for example, mixing with high shearing stress, and the use of microwaves or ultrasound.

In a further preferred embodiment of the process according to the invention, the clear crude inulin solution can be subjected to a targeted cooling crystallization process which involves a defined cooling rate and the use of seed crystals.

However, it is also possible to simply prepare the suspension by stirring the crude inulin into water and stirring the mixture for several hours at the desired temperature.

In the process according to the invention, it is not necessary for the crude inulin to be present in dry form; the salt-free extract, which is obtained as intermediate in the preparation of the crude inulin, is also suitable as raw material.

If required, the pH of the crude inulin suspension is adjusted to the pH optimum of the enzyme to be used. In the case of inulinase (for example SP 230 by NOVO, which has an activity of 3000 inulinase units (INU)/g), this value is 4.5–5.0.

Suitable enzymes are, in the case of inulin, hydrolases, such as inulinases, exo-inulinases or β-invertases. If appropriate, a combination of various hydrolases can also be used.

The reaction temperature depends, on the one hand, on the stability of the enzymes used to high temperatures and, on the other hand, on the dry matter content of the crude inulin suspension. As a rule, the temperature is kept constant at between 30°–70° C., depending on the dry matter content.

However, it can also be advantageous to vary the temperature during the reaction too, for example to reduce it as the medium-length chain content decreases, or to increase it to reduce the viscosity of the solution.

The dosage rate of enzyme per kg of crude inulin depends on the short-chain oligosaccharide content, the reaction temperature and the intended reaction time. In the case of inulinase, 500–4000 inulinase units are required per kg of crude inulin at 50°–60° C., depending on the reaction time available.

The reaction itself proceeds with stirring and pH monitoring.

To terminate the enzymatic activity, either the pH can be raised to 7.5–8.5 and/or only the temperature can be raised to 90°–95° C. With a view to the chromatographic separation which follows, it has shown to be advantageous to raise the temperature and to subsequently hold it for 20–30 minutes.

The resulting clear solution can immediately be separated chromatographically by a method known per se. If the separation is carried out on strongly acidic cation exchanger resins which are loaded with $Ca^{2+}$, the sequence of elution is: long-chain inulin, glucose and fructose.

Instead of by means of chromatography, the long-chain inulin can also be removed using a decanting centrifuge or by means of another, known separation process. In this case, the enzymatic reaction is terminated not by raising the temperature, but merely by raising the pH. When the enzymatic reaction has ended as a result of raising the pH, the long-chain inulin, which is in suspended form, can also be separated from the dissolved, low-molecular-weight components by means of filtration in suitable apparatuses, such as, for example, pressure filters.

Since the clear solution obtained after the enzymatic reaction contains, besides long-chain inulin, essentially only fructose, glucose and sucrose, the long-chain inulin can also be removed by means of ultrafiltration. Only the use of relatively simple and therefore economical membranes is necessary because only mono- and disaccharides are to be separated from molecules having a high degree of polymerization (DP>10).

The long-chain inulin obtained can be converted into a form with good storage stability by means of a drying process known per se (for example spray drying).

The process according to the invention allows long-chain inulin with a narrow range of variation with regard to chain length to be obtained. The mean chain length can be between 15 and 40, preferably 20–30, monomer units, depending on the reaction conditions chosen. The yield of long-chain inulin is 20–50% based on crude inulin and depends essentially on the content of inulin with desired chain length in the original raw material.

The resulting inulins are advantageously employed as a component in foodstuffs, also in conjunction with sweeteners, bulking agents, thickeners, stabilizers and the like, and as a fat substitute in foodstuffs, carbohydrate substitute, dietary fiber and, moreover, as an excipient for pharmacological active substances and as an indicator for kidney clearance.

EXAMPLE I

Mean Chain Length Determination

Inulin molecules are composed of a chain of fructose molecules having in each case a terminal glucose molecule. Complete enzymatic hydrolysis of inulin results in the formation of fructose and glucose, the ratio of fructose to glucose representing the mean chain length of the inulin.

1 g of the inulin test sample is dissolved in 100 cm$^3$ of 0.1M sodium acetate buffer, pH 5.0, by heating it for 20 minutes at 96° C. 10 cm$^3$ of this solution are incubated with 6 units of inulinase for 5 hours at 56° C.

The glucose and fructose formed can be determined by HPLC or enzymatically.

EXAMPLE 2

Preparation of Crude Inulin 100 kg of finely comminuted chicory roots with an inulin content of 14.5 kg are subjected to counter current extraction with 125 kg of water at 75° C. and a pH of 5.5. The pH of the extract is first brought to 10.0–12.0 by adding 1.24 kg of CaO and then to 8.5 by passing in $CO_2$. The precipitate formed, which is composed of $CaCO_3$ and the precipitated impurities, is removed by filtration.

The clear solution is demineralized by ion exchange on weakly acidic cationic ion exchangers and weakly alkaline anionic ion exchangers. The solution is subsequently first concentrated to a dry matter content of 35–40% (hereinafter termed liquid crude inulin) and then converted to dry form in a suitable drying apparatus (for example a spray dryer).
Yield: 10 kg of dry crude inulin
Mean chain length: 7–9

This procedure is not limited to processing chicory. Other plants, or part of plants, which contain inulin can also be processed in the same manner.

The examples which follow can be carried out either using dried crude inulin or demineralized extract which has been concentrated to a dry matter content of 35–40%, since both products are equally suitable as raw material for obtaining long-chain inulin.

EXAMPLE 3

Prior Art; Inulin Fractionation by Solvent Precipitation 2.25 kg of liquid crude inulin with a dry matter content of 40% or 0.9 kg of dry crude inulin are dissolved in 4.5 l, or 6.0 l, of water, respectively, and 4 l of isopropanol are added, with slow stirring. The precipitate is allowed to settle overnight. The supernatant is decanted off, and the precipitate is then removed by centrifugation. Isopropanol is recovered from the supernatant by distillation, water is used to adjust the isopropanol to 40%, and this is used for repeatedly washing the precipitate.

The washed precipitate is dried in vacuum overnight at 40° C.
Yield: 28% based on crude inulin employed
Mean chain length: 17

EXAMPLE 4

Prior Art; Inulin Fractionation by Ultra-filtration 20 g of dry crude inulin (or a corresponding amount of liquid crude inulin) were first diluted with 2 l of water and separated at room temperature in an ultrafiltration unit equipped with a membrane with a cut-off of 500 daltons. The retentate was diluted twice using in each case 600 cm$^3$ of water and subjected to ultrafiltration. Then, the retentate was evaporated to dryness.
Yield: 30% based on crude inulin employed
Mean chain length: 18

EXAMPLE 5

Prior Art; Inulin Fractionation by Crystallization 20 kg of dry crude inulin were suspended in 40 l of water and dissolved by heating the suspension to 80° C. (the corresponding amount of liquid crude inulin can be used directly), and the solution was then cooled slowly to 50° C. During this process, some of the inulin precipitated in solid form. A particle size determination revealed that the mean particle size was 20 ξm. Since this particle size is too small for separation in a perforated-basket centrifuge, the separation was carried out in a decanting centrifuge. The residue was washed with water at 50° C. and then dried.
Yield: 22% based on crude inulin employed
Mean chain length: 12

EXAMPLE 6

Prior art; Inulin Fractionation by Chromatography

A chromatography column of length 10 m and diameter 0.25 m, packed with a weakly - crosslinked, highly acidic cation exchanger resin loaded with $Ca^{2+}$ (for example Duolite® C 204), was brought to 60° C., 15 kg of crude inulin were applied in the form of a 40% by weight aqueous solution, and the column was eluted using demineralized water which had been rendered alkaline to pH 9.0 (using $Ca(OH)_2$). The effluent was cut in such a manner that a fraction with a DP of 5 and higher homologs and a second fraction with DP<5 were collected.

The fraction with DP>5 contained the long-chain inulin. This fraction was evaporated to dryness. The yield and mean chain length of this product depend on where the cut was made.
Yield: 25–35% based on crude inulin employed
Mean chain length: 12–16

EXAMPLE 7

16 kg of dry crude inulin were suspended in 24 l of water in a thermostatically controllable stirred vessel (a corresponding amount of liquid crude inulin can be used directly), and brought to 50° C., with stirring. After a residence time of 8 h, the pH was brought to 4.8–5.0, and 18 ml of inulinase (NOVO, SP 230) were added. During an incubation time of 24 hours, the temperature and the pH were kept constant at 50° C. and 4.8–5.0, respectively.

The enzymatic reaction was terminated by heating the suspension to 95° C., and the suspended particles were simultaneously dissolved. The clear solution was chromatographed using a chromatography apparatus as described in Example 6. The fraction containing long-chain inulin was evaporated to dryness.
Yield:
long-chain inulin: 4.8 kg=30% based on crude inulin
fructose: 8.8 kg=55% based on crude inulin
mean chain length: 16

EXAMPLE 8

16 kg of dry crude inulin were suspended in 16 l of water in a thermostatically controllable stirred vessel (a corresponding amount of liquid crude inulin can be used after concentration to a dry matter content of 50%), and the suspension was first heated to 80°–90° C., with stirring, and so dissolved. The temperature was then reduced stepwise to 60 degree, and the resulting suspension was kept at this temperature for 16 hours. After the pH had been brought to 4.8–5.0, 18 ml of inulinase (NOVO, SP 230) were added to the suspension, and this was incubated for 24 h at 60° C. and a pH of 4.8–5.0 with stirring.

The enzymatic reaction was terminated by heating the suspension to 95° C., and the suspended particles were simultaneously dissolved.

The clear solution was separated by chromatography as described in Example 6. The fraction containing long-chain inulin was evaporated to dryness, while only concentrations of the dry matter content of up to 70% were necessary in the case of the fructose fraction. The mean chain length of the inulin product and the yield obtained depend on the temperature and the time of the enzymatic reaction.
Yield:
long-chain inulin: 30–45% of the crude inulin employed
Fructose: 45–60% of the crude inulin employed
mean chain length: 25–40

EXAMPLE 9

A batch as described in Example 8 was treated enzymatically. The enzymatic reaction was terminated by rendering the mixture alkaline; pH 8.5.

The suspension was separated at 60° C. using an ultrafiltration apparatus and a membrane with a cut-off of 500 daltons. The permeate was concentrated and used for obtaining fructose. The retentate, which contains long-chain inulin, was evaporated to dryness.
Yield:
long-chain inulin: 30–45% of the crude inulin employed
fructose: 45–60% of the crude inulin employed
mean chain length: 25–40.

We claim:

1. A process for the preparation of long-chain inulin having an average chain length greater than 20 monomer units while simultaneously obtaining glucose and fructose, which comprises contacting an aqueous crude inulin suspension having a crude inulin concentration of 20–70% by weight with inulinase at temperatures of 30°–70° C. so as to degrade short-chain components of the crude inulin having chain lengths of up to 10 monomer units to mono- and disaccharides, separating off the long-chain inulins from the mono- and disaccharides in the resulting suspension and then converting the long chain inulins into dry form.

2. The process as claimed in claim 1, wherein the crude inulin concentration is 40–50% by weight.

3. The process as claimed in claim 1 wherein the crude inulin suspension is heated at 80°–95° C. before being contacted with the inulinase, then the resulting heated suspension is brought to 30°–70° C., and held during the contacting at a constant temperature of between 30° and 70° C.

4. The process as claimed in claim 3 wherein during the contacting the resulting suspension is maintained at a pH of 4.5 to 5.0.

5. The process as claimed in claim 4 wherein the degrading is terminated after a reaction time of 2–48 h by raising the pH to 8.0 to 9.0 or by heating the mixture to 90°–100° C.

6. The process as claimed in claim 1 wherein the long-chain inulins are separated from the mono- and disaccharides in the suspension resulting from contacting with inulinase by crystallization by cooling and centrifugation and the long chain inulins are then converted into dry form.

7. The process as claimed in claim 1 wherein the suspension resulting from contacting with inulinase is converted into a clear solution by heating and the solution is then separated chromatographically using a strongly acidic cation exchange resin which is loaded with $Ca^{2+}$ to obtain a pure fructose fraction, a glucose/fructose mixed fraction, and a long-chain inulin fraction, and the fraction containing long-chain inulin is then converted into dry form.

8. The process of claim 1 wherein the suspension resulting from contacting with inulinase is diluted to produce a solution and the solution is separated by ultrafiltration to give a mono- and disaccharide fraction and a long-chain inulin fraction, and the fraction containing long-chain inulin is converted into dry form.

9. An inulin prepared by the process of claim 1, having a mean chain length of from greater than 20 to 30 monomer units.

* * * * *